(12) United States Patent
Wittke

(10) Patent No.: US 10,987,181 B2
(45) Date of Patent: Apr. 27, 2021

(54) HANDLING DEVICE FOR A MICROINVASIVE MEDICAL INSTRUMENT

(71) Applicant: Karl Storz SE & Co. KG, Tuttlingen (DE)

(72) Inventor: Uwe Wittke, Bad Dürrheim (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 40 days.

(21) Appl. No.: 16/153,065

(22) Filed: Oct. 5, 2018

(65) Prior Publication Data

US 2019/0159855 A1    May 30, 2019

(30) Foreign Application Priority Data

Oct. 24, 2017    (DE) ................... 10 2017 124 775.0

(51) Int. Cl.
| | | |
|---|---|---|
| A61B 34/00 | (2016.01) | |
| A61B 17/00 | (2006.01) | |
| H01R 13/11 | (2006.01) | |
| A61B 18/00 | (2006.01) | |
| H01R 13/24 | (2006.01) | |

(52) U.S. Cl.
CPC ........ *A61B 34/72* (2016.02); *A61B 17/00234* (2013.01); *A61B 18/00* (2013.01); *H01R 13/111* (2013.01); *A61B 2017/0042* (2013.01); *A61B 2017/0046* (2013.01); *A61B 2017/00345* (2013.01); *A61B 2017/00411* (2013.01); *A61B 2017/00464* (2013.01); *A61B 2018/00077* (2013.01); *A61B 2018/00178* (2013.01); *H01R 13/2442* (2013.01); *H01R 2201/12* (2013.01)

(58) Field of Classification Search
CPC .. A61B 34/72; A61B 17/00234; H01R 13/111
See application file for complete search history.

(56) References Cited

U.S. PATENT DOCUMENTS

| | | | |
|---|---|---|---|
| 7,587,244 B2* | 9/2009 | Olbertz | A61N 1/3752 |
| | | | 607/37 |
| 2016/0256232 A1* | 9/2016 | Awtar | A61B 34/75 |
| 2017/0333115 A1* | 11/2017 | Schwarz | A61B 17/28 |

FOREIGN PATENT DOCUMENTS

| | | |
|---|---|---|
| CN | 201529146 U | 7/2010 |
| DE | 9190051.4 U1 | 6/1993 |
| DE | 4323584 A1 | 1/1995 |
| DE | 19512640 C2 | 10/1996 |
| DE | 10317038 A1 | 10/2003 |
| DE | 202007000428 U1 | 4/2007 |
| DE | 102014116065 A1 | 5/2016 |
| EP | 2303170 B1 | 3/2017 |

* cited by examiner

*Primary Examiner* — Gary Jackson
*Assistant Examiner* — Anant A Gupta
(74) *Attorney, Agent, or Firm* — McGlew and Tuttle, P.C.

(57) ABSTRACT

A manipulation device (20) for a microinvasive medical instrument (10) comprises a recess (47) for receiving a proximal region (72) of an electrically conductive transmission device (70) for transmitting electrical power and at least either a force or a torque to a distal end of a microinvasive medical instrument (10), and a contacting device (50) for producing an electrical contact to a transmission device (70) arranged in the recess (47). The contacting device (50) has a plurality of contact faces (57) for simultaneously bearing on a surface (75) of a transmission device (70) arranged in the intended manner in the recess (47).

20 Claims, 2 Drawing Sheets

Fig. 3   III-III
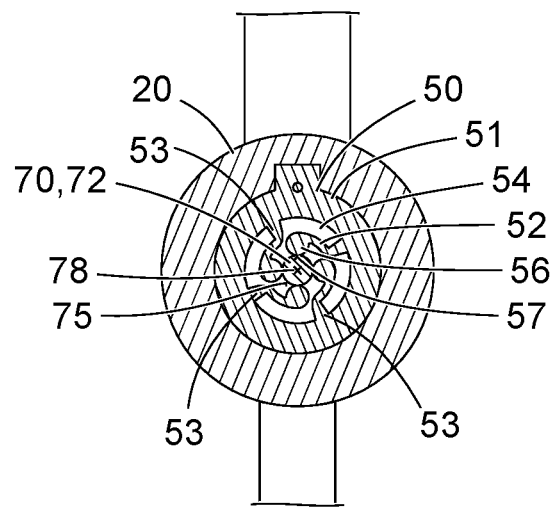
Fig. 4
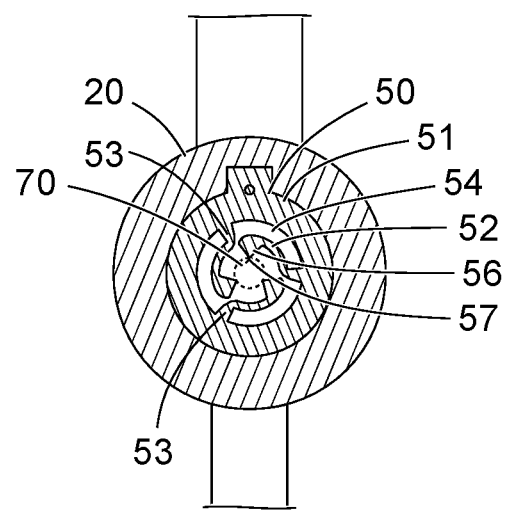
Fig. 5
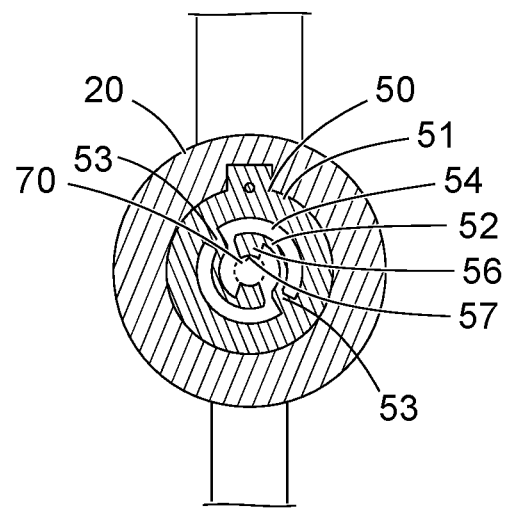

HANDLING DEVICE FOR A MICROINVASIVE MEDICAL INSTRUMENT

CROSS REFERENCE TO RELATED APPLICATIONS

This application claims the benefit of priority under 35 U.S.C. § 119 of German Application 10 2017 124 775.0, filed Oct. 24, 2017, the entire contents of which are incorporated herein by reference.

TECHNICAL FIELD

The present invention relates to a manipulation device for a microinvasive medical instrument, and to a microinvasive medical instrument having such a manipulation device.

BACKGROUND

A typical microinvasive medical instrument comprises a manipulation device at its proximal end, a long and generally thin shaft, which extends from the proximal end to the distal end of the instrument, and a tool or another effecting device for grasping, squeezing, coagulating, cutting, punching or for other effects at the distal end of the instrument. One or more transmission devices for transmitting a force and/or a torque from the manipulation device at the proximal end to the effecting device at the distal end run within the shaft. In microinvasive medical instruments having an electrosurgical function, in particular in bipolar electrosurgical microinvasive medical instruments, the transmission device is often also involved in transmitting electrical power from the proximal end to the distal end.

High-quality microinvasive medical instruments are generally re-usable. To make them easier to clean after use, and to permit replacement of a faulty component and an alternative use of different components (for example different effecting devices, or shafts of different length), a high-quality microinvasive medical instrument is generally able to be dismantled. In the case of an instrument which can be dismantled, and in which the transmission device is also involved in transmitting electrical power, a mechanically separable electrical contact to the transmission device has to be produced in particular at the proximal end of the instrument.

DE 43 23 584 A1 describes a medical instrument that can be dismantled and that has an electrode tube 11. A contact spring 22 bears electrically conductively at the rear end of the electrode tube in the axial direction and is connected electrically conductively to a high-voltage lead 23 (column 3, lines 11 to 14).

DE 91 90 051.4 U1 describes a handpiece 1 which is able to perform electrosurgical cutting (second last paragraph on page 7). An electrically conductive connection to a tool 6 (FIG. 1) is established via an electrically conductive terminal 17, an electrically conductive metal band 18 and an electrically conductive O-ring 19 (last paragraph on page 10; FIG. 2).

DE 195 12 640 C2 describes a surgical endoscopy instrument with a working electrode. A manipulation part 2 of the endoscopy instrument has two mutually insulated contact springs 18 which each electrically contact a respective corresponding contact piece 14 at the proximal end of a shaft part 1 to be connected to the manipulation part 2 (column 3, lines 20 to 24; figures).

DE 103 17 038 A1 describes an electrosurgical instrument. A power cord 22 comprises a wire 56 which is bonded to a first electrode contact 60, and wire 58 which is bonded to a second electrode contact 62 (column 5, lines 25 to 30; FIG. 5).

CN 201529146 U describes an electrosurgical instrument. A contact pin 15 touches a proximal end of a shaft (FIG. 2).

EP 2 303 170 B1 describes a catheter arrangement. A manipulation device has a plurality of contacts 146 or set screws 148 which each make electrical contact with a ring contact 150 (paragraphs [0026], [0033]; FIGS. 7 and 8).

SUMMARY

An object of the present invention is to provide an improved manipulation device and an improved microinvasive medical instrument, which manipulation device in particular permits a reliable electrical contact to a transmission device of the microinvasive medical instrument.

A manipulation device for a microinvasive medical instrument comprises proximal region portion defining a recess for receiving a proximal region of an electrically conductive transmission device for transmitting electrical power or an electrical signal and at least either a force or a torque to a distal end of a microinvasive medical instrument, and a contacting device for producing an electrical contact to a transmission device arranged in the recess, wherein the contacting device has a plurality of contact faces for simultaneously bearing on a surface of a transmission device arranged in the intended manner in the recess.

The manipulation device is provided and configured to form a microinvasive medical instrument together with a shaft, in particular an outer shaft, a transmission device (and optionally further transmission devices), and a tool or another effecting device. The manipulation device thus forms one of several components of a microinvasive medical instrument. The shaft, the transmission device, the effecting device and, if appropriate, further components of the microinvasive medical instrument are in particular not part of the manipulation device.

The manipulation device may comprise, in particular, a stationary component for mechanical connection to a proximal end of an outer shaft or of another shaft for a microinvasive medical instrument. In particular, the stationary part is mechanically connected or connectable to a shaft in such a way as to be releasable non-destructively or in such a way as to be releasable non-destructively even without using a tool. Alternatively, the stationary component is connectable or connected to a shaft in such a way that it is not releasable non-destructively or in such a way that it is releasable non-destructively only by using a tool. In particular, the stationary component is stationary to the extent it is mechanically connectable or connected to a shaft rigidly or in such as way as to be rotatable relative to the shaft about the longitudinal axis thereof.

Moreover, the manipulation device may comprise, in particular, a component which is manually movable relative to the stationary component, for example a component pivotable about a pivot axis. The pivot axis is in particular orthogonal to the longitudinal axis of a shaft connected in the intended manner to the manipulation device. The manually movable component is provided and configured for mechanical coupling to a transmission device for a microinvasive medical instrument in such a way as to be releasable non-destructively and in particular in such a way as to be releasable without using a tool. Alternatively, the manually movable component is coupled to the transmission device in such a way that it is not releasable non-destructively or in such a way as be releasable non-destructively only by using a tool.

The recess (the proximal region portion defining the recess) for receiving a proximal region of a transmission device may be arranged and configured such that the proximal end of the transmission device protrudes proximally from the manipulation device, in particular from the stationary component thereof. The region of a transmission device to be received by the recess does not therefore have to comprise the proximal end of the transmission device but is located near the proximal end of the transmission device. The cross section of the recess for receiving the proximal region of the transmission device is in particular adapted to the cross section of the proximal region of the transmission device.

Moreover, the manipulation device comprises in particular a recess for receiving a proximal region of a shaft. The recess for receiving a proximal region of a shaft and the recess for receiving a proximal region of a transmission device lead into each other in particular. The cross section of the recess for receiving the proximal region of the shaft is in particular adapted to the cross section of the proximal region of the shaft. The cross section of the recess for receiving a proximal region of a shaft is in particular larger than the cross section of the recess for receiving a proximal region of a transmission device.

The contacting device is in particular arranged in the recess for receiving a proximal region of a transmission device or in a for example annular extension of the recess. A contact face of the contacting device is a surface region of the contacting device which bears directly on a corresponding surface region of the transmission device in the intended use of the manipulation device, in particular with the intended arrangement of a transmission device, provided for combination with the manipulation device, in the recess of the manipulation device. The contact faces of the contacting device are spaced apart from each other.

The manipulation device is in particular provided and configured for a predetermined shape of a transmission device, or for a transmission device with predetermined properties at least of the proximal region of the transmission device, and is adapted to said shape or properties. The manipulation device is provided and configured in particular for a predetermined shape of a shaft, or for a shaft with predetermined properties at least of the proximal region of the shaft, and is adapted to said shape or properties.

A plurality of contact faces of the contacting device of the manipulation device can improve the reliability of the electrical contact to the transmission device and can reduce the electrical contact resistance. Even if one of the contact faces corrodes, deforms or is otherwise damaged, further contact faces of the contacting device can permit reliable electrical contacting of the transmission device.

In a manipulation device as described here, in particular all of the contact faces are configured to bear in a radial direction on a surface of a transmission device arranged in the recess.

A direction is radial when it is orthogonal to the longitudinal axis of a transmission device arranged in the intended manner in the recess of the manipulation device. A contact face bears on the surface of the transmission device in a radial direction when the normal force between the contact face and the surface of the transmission device and therefore the surface normals of the contact face and of the surface of the transmission device are oriented in the radial direction.

In a manipulation device as described here, in particular the surface normals of all the contact faces are oriented radially.

Contact faces bearing in a radial direction, or contact faces whose surface normals are arranged in the radial direction, do not exert on a transmission device, arranged in the intended manner in the recess of the manipulation device, any axial force or any force parallel to the longitudinal axis of the transmission device or any torque about the longitudinal axis of the transmission device. The contact faces do not therefore influence or impede the transmission of a force or of a torque by means of the transmission device.

In a manipulation device as described here, in particular all of the contact faces are electrically connected in parallel.

Several contact faces electrically connected in parallel can improve the reliability of the electrical contact and reduce the contact resistance.

In a manipulation device as described here, in particular all of the contact faces of the contacting device may intersect a plane orthogonal to the longitudinal axis of a transmission device arranged in the intended manner in the recess.

An arrangement of the contact faces in such a way that all of the contact faces intersect a plane orthogonal to the longitudinal axis of the transmission device can avoid the generation of a torque about an axis orthogonal to the longitudinal axis of the transmission device caused by the pressing forces of the contact faces. Moreover, such an arrangement of the contact faces can reduce the installation space of the contacting device in a direction parallel to the longitudinal axis of the transmission device.

In a manipulation device as described here, angle distances between adjacent contact faces of the contacting device may be identical.

In particular, all the angle distances between in each case two adjacent contact faces of the contacting device are identical. The angles are always with reference to the longitudinal axis of a transmission device arranged in the intended manner in the recess of the manipulation device.

In a manipulation device as described here, in particular two contact faces may be arranged at mutual angle distances of 180 degrees, or three contact faces may be arranged at mutual angle distances of 120 degrees, or four contact faces are arranged at mutual angle distances of 90 degrees, or five contact faces may be arranged at mutual angle distances of 72 degrees.

All angles are with reference to the longitudinal axis of a transmission device arranged in the intended manner in the recess and contacted by the contacting device of the manipulation device. The angle distance of two adjacent contact faces signifies the angle distance between the area centroids of the contact faces.

A uniformly distributed arrangement of the contact faces over the circumference of the transmission device can have the effect that the forces exerted on the transmission device by the contact faces counterbalance each other.

In a manipulation device as described here, the contacting device may be in particular of a monolithic configuration.

The contacting device may be formed from a single workpiece (in particular of metal), for example by casting, milling, etching or by other means.

In a manipulation device as described here, in particular all of the contact faces may be formed on one and the same monolithically configured element.

In a manipulation device as described here, in particular at least one of the contact faces may be movable in a substantially radial direction.

In particular, each contact face of the contacting device is movable in a substantially radial direction. A contact face is movable in a substantially radial direction if the contact face or its area centroid is movable along a path which encloses a small angle with a straight line which passes through the area centroid of the contact face and is orthogonal to the longitudinal axis of a transmission device arranged in the intended manner in the recess. An angle is small if it is not more than 30 degrees or not more than 20 degrees or not more than 10 degrees or not more than 5 degrees. The contact face or the contact faces are movable in a substantially radial direction in particular counter to a restoring force of an elastic structure.

In a manipulation device as described here, the contacting device may have in particular a plurality of resilient tongues, each contact face being arranged at a resilient tongue.

In particular, a single contact face may be formed at each resilient tongue. Each contact face is in particular arranged at a free end of a resilient tongue, of which the other end is rigidly connected to the rest of the contacting device.

In a manipulation device as described here, the resilient tongues of the contacting device may each extend in particular parallel or substantially parallel to a plane orthogonal to the longitudinal axis of a transmission device arranged in the intended manner in the recess.

Resilient tongues, each extending parallel to a plane orthogonal to the longitudinal axis of the transmission device, can permit a particularly compact design of the contacting device, in particular a contacting device that is especially short in a direction parallel to the longitudinal axis of the transmission device.

In a manipulation device as described here, the resilient tongues of the contacting device may each extend in particular parallel or substantially parallel to a surface of a transmission device arranged in the intended manner in the recess.

The resilient tongues may each extend in particular parallel to an annular surface region of the transmission device on which the contact faces bear.

In a manipulation device as described here, the resilient tongues of the contacting device may be in particular each formed at least in part in the shape of an arc of a circle or substantially in the shape of an arc of a circle.

A design of the resilient tongues in the shape of an arc of a circle can permit a compact design of the contacting device.

In a manipulation device as described here, in particular each contact face may have a length substantially greater than its width.

The length of a contact face is measured in a direction parallel to the longitudinal axis of a transmission device arranged in the intended manner in the recess. The width of a contact face is measured in a direction orthogonal thereto, in particular in a direction of the circumference of a transmission device arranged in the intended manner in the recess. The length of the contact face is in particular greater than its width, at least by a factor of five or at least by a factor of two or at least by a factor of twenty. The dimensions of the contact faces refer in particular to their dimensions immediately after their production and prior to delivery and use.

In a manipulation device as described here, in particular each contact face may have a length not greater than its width.

The length of a contact face may be in particular not more than two thirds or not more than a half or not more than a third or not more than a quarter of the width of the contact face.

In a manipulation device as described here, the contacting device may be in particular moreover provided and configured to center a proximal region of a transmission device inserted in the intended manner into the manipulation device.

The contacting device centers the proximal region of the transmission device, particularly to the extent that it guides said proximal region with respect to radial movements. The contacting device in particular provides an elastic force counter to any deviation of the transmission device from a desired position. This force is generated, for example, by the described resilient tongues.

A medical instrument comprises a manipulation device, as described here, a shaft, of which the proximal end is mechanically connected or connectable to the manipulation device, and a transmission device for transmitting electrical power and at least either a force or a torque from the manipulation device to a distal end of a microinvasive medical instrument to form the manipulation device.

A proximal region of the shaft can be arranged in a corresponding recess of the manipulation device. A proximal region of the transmission device can be arranged in the corresponding recess provided for the transmission device in the manipulation device.

Embodiments are explained in more detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a schematic view of a further section through the medical instrument from FIGS. 1 and 2;

FIG. 4 is a schematic view of a section through a manipulation device;

FIG. 5 is a schematic view of a section through a further manipulation device.

DESCRIPTION OF PREFERRED EMBODIMENTS

Figure 1:
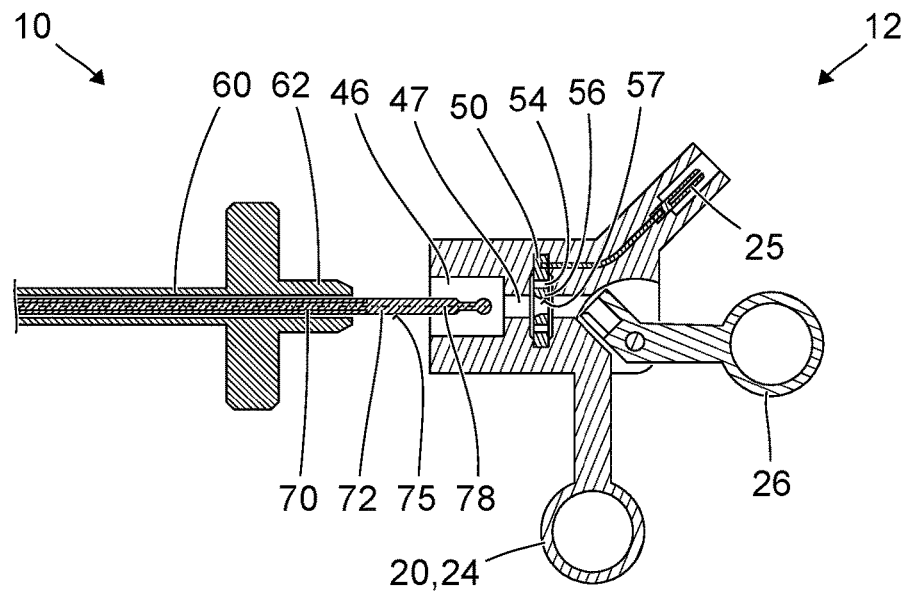
FIG. 1 is a schematic view of a section through components of a medical instrument.

Referring to the drawings, FIG. 1 shows a schematic view of a section through components of a microinvasive medical instrument 10. In particular, FIG. 1 shows components that form a proximal region 12 of the instrument 10. The distal end of the instrument 10, with a tool or another effecting device for grasping, squeezing, holding, cauterizing, cutting, punching and/or for another action, is located outside the region shown, namely to the left of the region shown. The section plane shown in FIG. 1 is parallel to a longitudinal direction of the instrument 10, arranged horizontally in FIG. 1.

The instrument 10 comprises, in its proximal region 12, a manipulation device 20 with a stationary component 24, at which an electrical plug-in contact 25 is arranged for supplying electrical power for electrosurgical measures. The manipulation device 20 further comprises a manually movable component 26, which is pivotable relative to the stationary component 24 about a pivot axis orthogonal to the drawing plane of FIG. 1. The stationary component 24 and the movable component 26 each have an eye through which one or more fingers of a hand can be guided.

The instrument 10 moreover comprises a shaft 60 with a proximal end 62, and a transmission device 70 for transmitting electrical power and/or an electrical signal and also a force and/or a torque to the distal end (not shown in the figure) of the instrument 10. The transmission device 70 has a proximal region 72. The instrument 10 is shown in FIG. 1 in a configuration in which the proximal end 62 of the shaft 60 and the proximal region 72 of the transmission device 70 are not yet mechanically connected to the manipulation device 20 and, consequently, the instrument 10 is not usable. A longitudinal axis 78 of the transmission device 70 lies in the section plane shown in FIG. 1.

The manipulation device 20 has a first, distally open recess 46 for receiving the proximal end 62 of the shaft 60. The cross section of the first recess 46 (in a plane orthogonal to the longitudinal axis 78 of the transmission device 70 and thus orthogonal to the section plane shown in FIG. 1) and the cross section of the proximal region 62 of the shaft 60 correspond in such a way that the proximal region 62 of the shaft 60 can be inserted with low friction into the first recess 46 and can then be held with minimal play in the first recess 46. In particular, the cross sections of the first recess 46 in the manipulation device 20 and of the proximal end 62 of the shaft 60 are each circular or substantially circular, such that the shaft 60 can be rotated relative to the manipulation device 20 about the longitudinal axis 78 of the transmission device 70. A locking device for locking the proximal end 62 of the shaft 60 in the first recess 46 is not shown in FIG. 1.

The manipulation device 20 moreover has a second recess 47, which is arranged proximally with respect to the first recess 46 and directly adjoins the first recess 46. The cross section of the second recess 47 (in a plane orthogonal to the longitudinal axis 78 of the transmission device 70) and the cross section of the proximal region 72 of the transmission device 70 correspond in such a way that the proximal region 72 of the transmission device 70 can be inserted into the second recess 47 starting from the configuration shown in FIG. 1.

The manipulation device 20 moreover has a contacting device 50 with contact regions 56. The contacting device 50 is arranged in a substantially annular extension of the second recess 47. In the section plane shown in FIG. 1, each contact region 56 is separated from the rest of the contacting device 50 by a gap 54. Each contact region 56 forms a contact face 57 for the electrical contacting of a corresponding surface region 75 of the proximal region 72 of the transmission device 70. The contacting device 50 is connected electrically conductively to the plug-in contact 25 at the manipulation device 20.

Figure 2:
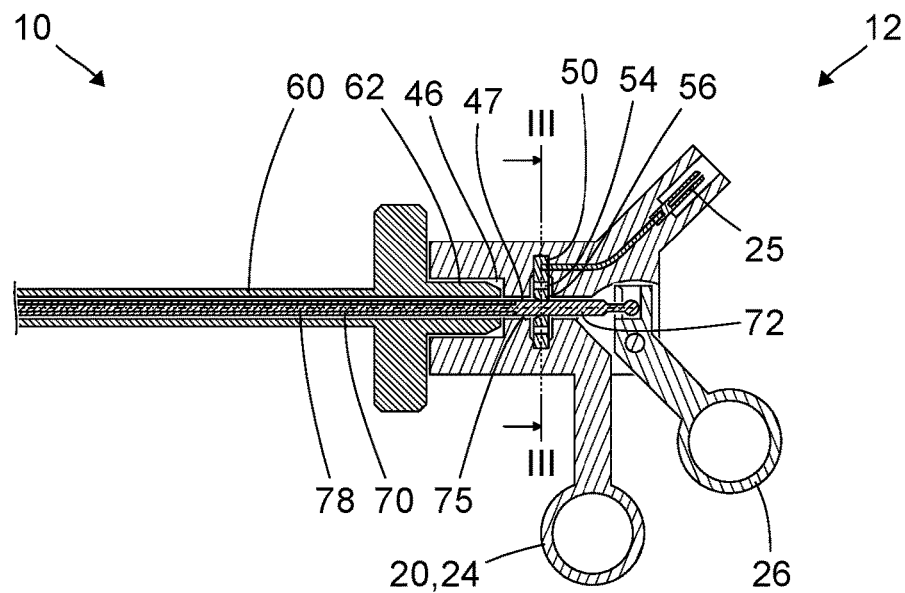
FIG. 2 is a further schematic view of a section through the components of the medical instrument from FIG. 1.

FIG. 2 shows a schematic view of a section through the proximal region 12 of the medical instrument 10 shown in FIG. 1. The section plane of FIG. 2 corresponds to the section plane of FIG. 1.

The configuration shown in FIG. 2 differs from the configuration of the instrument 10 shown in FIG. 1 in that the proximal region 62 of the shaft 60 is inserted into the first recess 46 of the manipulation device 20 and the proximal region 72 of the transmission device 70 is inserted into the second recess 47 of the manipulation device 20. The proximal region 62 of the shaft 60 is locked in the first recess 46 of the manipulation device 20 by the aforementioned locking device (not shown in FIGS. 1 and 2).

In the configuration shown in FIG. 2, the proximal end of the transmission device 70 is mechanically coupled to the movable component 26 of the manipulation device 20 in such a way that a pivoting movement of the movable component 26 relative to the stationary component 24 of the manipulation device 20 is associated with a translational movement of the transmission device 70 relative to the shaft 60 parallel to the longitudinal axis 78 of the transmission device 70.

In the configuration shown in FIG. 2, the contact faces 57 of the contact regions 56 of the contacting device 50 bear at at least two locations, lying opposite each other in the example shown, on the surface region 75 of the proximal region 72 of the transmission device 70 and thus establish an electrical contact.

FIG. 3 shows a schematic view of a further section through the instrument 10 from FIGS. 1 and 2, in an illustrative configuration of the contacting device 50. The section plane III-III of FIG. 3 is orthogonal to the longitudinal axis 78 of the transmission device 70 and orthogonal to the section planes of FIGS. 1 and 2. The section plane III-III intersects the contacting device 50. The position of the section plane III-III of FIG. 3 is indicated in FIG. 2.

In its embodiment shown in FIG. 3, the contacting device 50 has four contact regions 56. In the section plane III-III of FIG. 3, each contact region 56 has a substantially circular cross section and is arranged at a free end of a resilient tongue 52 substantially in the shape of an arc of a circle. Each resilient tongue 52 is separated from an annular region (annular portion) 51 of the contacting device 50 by a gap 54. The contact regions 56 and the resilient tongues 52 are arranged within the annular region 51. The end of each resilient tongue 52 facing away from the contact region 56 is rigidly connected mechanically to the annular region 51 of the contacting device 50 at an annular portion joining region 53.

The contacting device 50 is of a monolithic configuration, i.e. the annular region 51, the resilient tongues 52 and the contact regions 56 are formed from a single workpiece made of a metal, or of another electrically conductive material, by casting, milling, cutting, etching or by other means.

By virtue of the circular cross sections of the contact regions 56 and the circular cross section of the proximal region 72 of the transmission device 70, the contact faces 57 (cf. FIGS. 1 and 2) bearing directly on the circular cylindrical surface region 75 of the transmission device 70 are linear and, in the cross section shown in FIG. 3, punctiform. Wear of the contact regions 56 may cause a widening of the contact faces.

FIG. 4 shows a schematic view of a section through a manipulation device 20 for a medical instrument which, in terms of certain features, properties and functions, is similar to the manipulation device 20 of the instrument shown in FIGS. 1 to 3. The section plane of FIG. 4 corresponds to the section plane of FIG. 3. Features, properties and functions that distinguish the manipulation device 20 shown in FIG. 4 from the manipulation devices shown in FIGS. 1 to 3 are in particular described below.

The contacting device 50 of the manipulation device 20 shown in FIG. 4 has three contact regions, each with a contact face 57. The contact regions 56 are distributed uniformly over the circumference (indicated by a broken line in FIG. 4) of a transmission device inserted in the intended manner into the manipulation device 20. The angle between in each case two adjacent contact regions 56 is 120 degrees.

The contacting device 50 of the manipulation device 20 shown in FIG. 4 moreover differs from the contacting device of the manipulation device shown in FIGS. 1 to 3 in that the cross sections of the contact regions 56 are approximately triangular in the section plane of FIG. 4. Thus, each individual contact region 56, at least in the environment of its contact face 57, has a prismatic configuration with a triangular cross section.

FIG. 5 shows a schematic view of a section through a further manipulation device 20 which, in terms of certain features, properties and functions, is similar to the manipulation devices shown in FIGS. 1 to 4. The section plane of FIG. 5 corresponds to the section planes of FIGS. 3 and 4. Features, properties and functions that distinguish the manipulation device shown in FIG. 5 from the manipulation devices shown in FIGS. 1 to 4 are in particular described below.

The manipulation device shown in FIG. 5 differs from the manipulation devices shown in FIGS. 1 to 4 in particular in that the contacting device 50 has two contact regions 56. The contact regions 56 are arranged opposite each other, i.e. have an angle distance of 180 degrees.

The manipulation device 20 shown in FIG. 5 moreover differs from the manipulation devices shown in FIGS. 1 to 4 in that the contact faces 57 are not linear or narrow. Instead, the contact face 57 of each contact region 56 has a width (measured parallel to the circumference, indicated by a broken line in FIG. 5, of a transmission device 70 inserted into the manipulation device 20) which in particular is not smaller or not appreciably smaller than the length measured in a direction parallel to the longitudinal axis of the transmission device 70.

Features of the various embodiments of the contacting device 50 can be combined with each other in another way. In particular, a contacting device 50 can have two, three, five or more contact regions 56, each with a circular cross section (as shown in FIG. 3), or two, four or more contact regions 56 with a triangular cross section (as shown in FIG. 4), or three or more contact regions 56 with a wide, not just substantially linear contact face (as shown in FIG. 5). Moreover, a contacting device 50 can have a plurality of contact regions 56 with different cross sections.

The cross sections of the contact regions 56 can be constant over their entire length (measured in a direction parallel to the longitudinal axis 78 of a transmission device coupled in the intended manner to the manipulation device). Alternatively, the cross sections of the contact regions 56 can vary over their length. In particular, the contact regions 56 can, as indicated in FIGS. 1 and 2, have distally directed ramps or oblique surfaces or contours, which can make it easier to insert a transmission device into the contacting device 50.

While specific embodiments of the invention have been shown and described in detail to illustrate the application of the principles of the invention, it will be understood that the invention may be embodied otherwise without departing from such principles.

REFERENCE SIGNS 10 microinvasive medical instrument
12 proximal region of the microinvasive medical instrument 10
20 manipulation device of the microinvasive medical instrument 10
24 stationary component of the manipulation device 20, for mechanical connection to the proximal region 62 of the shaft 60
25 plug-in contact at the manipulation device
26 manually movable component of the manipulation device 20, for mechanical coupling to the proximal region 72 of the transmission device 70
46 first recess in the stationary component 24, for receiving the proximal region 62 of the shaft 60
47 second recess in the stationary part 24, for receiving the proximal region 72 of the transmission device 70
50 contacting device in the second recess 40, for electrical contacting of the surface region
75 of the proximal region 72 of the transmission device 70
51 annular region of the contacting device 50
52 resilient tongue of the contacting device 50
54 gap between the resilient tongue 52 and the rest of the contacting device 50
56 contact region of the contacting device 50
57 contact face at the contact region 56
60 shaft of the microinvasive medical instrument
62 proximal region of the shaft 60
70 transmission device of the microinvasive medical instrument
72 proximal region of the transmission device 70
75 surface region of the transmission device 70 provided to be contacted by the contact faces 57
78 longitudinal axis of the transmission device 70

The invention claimed is:

1. A manipulation device for a microinvasive medical instrument, the manipulation device comprising:
 a proximal region portion defining a recess for receiving a proximal region of an electrically conductive transmission device for transmitting electrical power and at least one of a force or a torque to a distal end of the microinvasive medical instrument; and
 a contacting device for producing an electrical contact to the electrically conductive transmission device arranged in the recess, wherein the contacting device comprises:
  a radially outward annular portion;
  a plurality of resilient tongues; and
  a plurality of contact faces for simultaneously bearing on a surface of the electrically conductive transmission device arranged in an intended position in the recess, wherein each contact face is arranged at a corresponding distal end of one of the resilient tongues and the resilient tongues each have a resilient tongue extent, from the radially outward annular portion to one of the contact faces, that is parallel to a plane orthogonal to a longitudinal axis of the electrically conductive transmission device arranged in the intended position in the recess.

2. The manipulation device according to claim 1, wherein the contact faces of the contacting device intersect the plane orthogonal to the longitudinal axis of the electrically conductive transmission device arranged in the intended position in the recess.

3. The manipulation device according to claim 1, wherein angle distances between adjacent contact faces of the contacting device are identical.

4. The manipulation device according to claim 1, wherein two contact faces are arranged at mutual angle distances of 180 degrees, or three contact faces are arranged at mutual angle distances of 120 degrees, or four contact faces are arranged at mutual angle distances of 90 degrees, or five contact faces are arranged at mutual angle distances of 72 degrees.

5. The manipulation device according to claim 1, wherein the contacting device is of a monolithic configuration.

6. The manipulation device according to claim 1, wherein the resilient tongues of the contacting device are each formed at least in part in a shape of an arc of a circle or with an arcuate shape.

7. The manipulation device according to claim 1, wherein each contact face has a length greater than a width thereof.

8. The manipulation device according to claim 1, wherein each contact face has a length not greater than a width thereof.

9. The manipulation device according to claim 1, wherein the contacting device is configured to center a proximal region of the electrically conductive transmission device inserted in the intended position into the manipulation device.

10. A medical instrument comprising:
a manipulation device comprising a proximal region portion defining a recess and a contacting device arranged in the recess, wherein the contacting device comprises:
a radially outward annular portion;
a plurality of resilient tongues; and
a plurality of contact faces, each of the contact faces being arranged at a distal end of a corresponding one of the resilient tongues;
a shaft, of which a proximal end is mechanically connected or connectable to the manipulation device;
an electrically conductive transmission device for transmitting electrical power and at least one of a force or a torque from the manipulation device to a distal end of the medical instrument to be formed with the manipulation device, the recess receiving a proximal region of the electrically conductive transmission device and the plurality of contact faces simultaneously bearing on a surface of the electrically conductive transmission device arranged in an intended position in the recess and the resilient tongues each have a resilient tongue extent, from the radially outward annular portion to one of the contact faces, that is parallel to a plane orthogonal to a longitudinal axis of the electrically conductive transmission device arranged in the intended position in the recess.

11. The medical instrument according to claim 10, wherein the contact faces of the contacting device intersect the plane orthogonal to longitudinal axis of the electrically conductive transmission device arranged in the intended position in the recess.

12. The medical instrument according to claim 10, wherein two contact faces are arranged at mutual angle distances of 180 degrees, or three contact faces are arranged at mutual angle distances of 120 degrees, or four contact faces are arranged at mutual angle distances of 90 degrees, or five contact faces are arranged at mutual angle distances of 72 degrees.

13. The medical instrument according to claim 10, wherein the contacting device is of a monolithic configuration.

14. The medical instrument according to claim 10, wherein the resilient tongues of the contacting device are each formed at least in part in a shape of an arc of a circle.

15. The medical instrument according to claim 10, wherein each contact face has a length greater than a width thereof.

16. The medical instrument according to claim 10, wherein each contact face has a length not greater than a width thereof.

17. The manipulation device according to claim 1, wherein each of the plurality of resilient tongues includes a resilient portion extending radially inwardly and circumferentially from an annular portion joining region to the contact faces, whereby each of the plurality of contact faces is a free end circumferentially offset from its associated annular portion joining region.

18. The medical instrument according to claim 10, wherein each of the plurality of resilient tongues includes a resilient portion extending radially inwardly and circumferentially from an annular portion joining region to the contact faces, whereby each of the plurality of contact faces is a free end circumferentially offset from its associated annular portion joining region.

19. A medical instrument comprising:
a manipulation device comprising a proximal region portion defining a recess and a contacting device arranged in the recess, wherein the contacting device comprises:
a radially outward annular portion;
a plurality of resilient tongues; and
a plurality of contact faces, each of the contact faces being arranged at a corresponding one of the resilient tongues;
a shaft, of which the proximal end is mechanically connectable to the manipulation device;
an electrically conductive transmission device mechanically connectable to the shaft for transmitting electrical power and at least one of a force and a torque from the manipulation device to a distal end of the medical instrument, the recess receiving a proximal region of the electrically conductive transmission device and the plurality of contact faces simultaneously bearing on a surface of the electrically conductive transmission device arranged in an intended position in the recess, wherein:
each of the resilient tongues includes a resilient portion extending radially inwardly and circumferentially, with a resilient portion extent from an annular portion joining region to the contact faces, whereby each of the plurality of contact faces is a free end circumferentially offset from its associated annular portion joining region; and
a plane orthogonal to a longitudinal axis of the electrically conductive transmission device, arranged in the intended position in the recess the contacting device, intersects each of the resilient tongues and each of the contact faces over the resilient portion extent.

20. The medical instrument according to claim 19, wherein:
each contact face has an axial length, along a direction of the longitudinal axis, not greater than a circumferential dimension thereof; and
each resilient tongue has an arcuate portion between the outward annular portion and the respective contact face.

* * * * *